(12) United States Patent
Reynolds et al.

(10) Patent No.: US 8,707,468 B2
(45) Date of Patent: Apr. 29, 2014

(54) PROTECTIVE GARMENT WITH TOURNIQUET

(75) Inventors: Rob Reynolds, Chelsea (CA); Chris Faust, Potsdam, NY (US); Magda Slobozianu, Ottawa (CA); Clint Hedge, Winchester (CA); Aristidis Makris, Ottawa (CA); Shaik Kalaam, Ottawa (CA); David Morton, Elkton, MD (US)

(73) Assignee: Med-Eng, LLC, Jacksonville, FL (US)

( * ) Notice: Subject to any disclaimer, the term of this patent is extended or adjusted under 35 U.S.C. 154(b) by 0 days.

(21) Appl. No.: 13/591,542

(22) Filed: Aug. 22, 2012

(65) Prior Publication Data

US 2013/0238014 A1   Sep. 12, 2013

Related U.S. Application Data

(63) Continuation-in-part of application No. 13/414,591, filed on Mar. 7, 2012, now Pat. No. 8,516,620.

(51) Int. Cl.
*A41D 1/06* (2006.01)

(52) U.S. Cl.
USPC .............................................................. 2/227

(58) Field of Classification Search
USPC ............ 2/79, 227, 2.5, 24, 228, 238, 247, 23, 2/69, 44, 310
See application file for complete search history.

(56) References Cited

U.S. PATENT DOCUMENTS

| 4,850,056 A | * | 7/1989 | Gardner et al. | 2/227 |
| 5,058,788 A | * | 10/1991 | Newmark | 224/222 |
| 5,865,782 A | * | 2/1999 | Fareed | 602/62 |
| 5,978,966 A | * | 11/1999 | Dicker et al. | 2/69 |

* cited by examiner

*Primary Examiner* — Tejash Patel
(74) *Attorney, Agent, or Firm* — Kane Kessler, P.C.; Paul E. Szabo

(57) ABSTRACT

A protective garment including a waist portion adapted to be donned proximate the waist of a wearer and first and second leg portions extending from a waist portion to at least proximate a knee portion of the wearer and a tourniquet member attached to an inner surface of at least one of said first and second leg portions.

23 Claims, 8 Drawing Sheets

PROTECTIVE GARMENT WITH TOURNIQUET

CROSS-REFERENCE TO RELATED APPLICATIONS

This application is a continuation-in-part of U.S. patent application Ser. No. 13/414,591, filed Mar. 7, 2012.

FIELD OF THE INVENTION

The invention relates to protective garments, and in particular, to protective garments having embedded tourniquet members, such as over garment protective shorts having embedded tourniquet members.

BACKGROUND OF THE INVENTION

Military personnel often work in hazardous environments and are frequently exposed to ballistic threats such as bullets and fragments from explosive devices such as bombs and roadside IEDs (improvised explosive devices). Personnel operating in these environments may be issued with a sleeveless protective jacket for wearing in combination with standard military uniform. The protective jacket comprises front and rear pockets each extending over the front and rear torso regions for receiving a ballistic resistant plate, typically composed of hard armor, as in a ceramic, with a composite of multiple layers of ballistic resistant fabric such as an aramid material and embedded epoxy resin which are heat pressed together. The front and rear protective plates assist in preventing bullets and fragments from damaging vital organs.

In more dangerous conditions, typically geared towards explosive device and bomb disposal applications, military personnel may be provided with suits including full body protective armour. These suits typically include a ballistic resistant plate that extends to cover the pelvic region of a wearer. These suits also typically include multiple layers of high strength fabric that provides protection below the groin region.

It has been discovered by the applicant, that the sleeveless protective jacket worn in combination with the standard military uniform does not provide sufficient protection below the pelvis and groin region of a wearer from projectiles, such as sand and other fragmentation debris resulting from the detonation of an explosive. This has caused serious injury to the pelvic and groin regions of armoured personnel. Accordingly, there is a need in the art for a protective garment that can be worn in combination with a sleeveless protective jacket, and that provides protection to the pelvic and/or groin regions of a wearer from projectiles While some prior art solutions have extended the ballistic resistant plate lower, this tends to impede movement. Other prior art solutions have provided for protective pants that attach directly to the bullet resistant plate or other underlying garments; this creates a barrier for the mobility of the wearer. Accordingly, there is a further need in the art for a protective garment that can be easily donned and doffed in combination with other protective military suits.

Prior art protective garments also suffer from the disadvantage of becoming effectively useless following an incident causing a leg injury. In this situation, it may be more critical to be able to doff the pants in a quick time to apply treatment options or otherwise manage blood loss. Accordingly, there is a further need in the art for protective pants that can facilitate post-incident injury treatment.

SUMMARY OF THE INVENTION

In accordance with a first embodiment of the present invention there is provided a protective garment, such as an over garment protective shorts including at least one pocket sized and otherwise dimensioned to removeably receive a ballistic protection panel therein and at least one ballistic protection panel configured to fit within each of the at least one pockets. The shorts are configured to be worn over existing pants and extend from a position covering the pelvic region of a wearer to a position proximate the knee region of the wearer.

According to an aspect of the invention, one or both of the leg portions of the protective shorts have incorporated therewith tourniquet members on an interior surface thereof. The one or more tourniquet members preferably include an inner webbing strap interwoven with an outer webbing strap that permits the tourniquet member to be tightened by reducing the circumference of the inner webbing strap with respect to the outer webbing strap.

Other advantages, features and characteristics of the present invention, as well as methods of operation and functions of the related elements of the structure, and the combination of parts and economies of manufacture, will become more apparent upon consideration of the following detailed description and the appended claims with reference to the accompanying drawings, the latter of which is briefly described hereinbelow.

BRIEF DESCRIPTION OF THE DRAWINGS

The novel features which are believed to be characteristic according to the present invention, as to its structure, organization, use and method of operation, together with further objectives and advantages thereof, will be better understood from the following drawings in which a presently preferred embodiment of the invention will now be illustrated by way of example. It is expressly understood, however, that the drawings are for the purpose of illustration and description only, and are not intended as a definition of the limits of the invention. In the accompanying drawings.

DETAILED DESCRIPTION OF THE PREFERRED EMBODIMENTS

The invention provides for an over garment protective shorts designed to be used in combination with a protective vest or other tactical personnel protection system for protecting against a variety of threats. The over garment protective shorts according to the invention is designed to be worn on top of standard combat pants, but may also be worn underneath other protective garments as well. In particular, the over garment protective shorts according to the invention are provided to protect a wearer from blast fragments such as sand, soil or other debris, resulting from an indirect hazardous event occurring in a region surrounding the wearer. These hazardous events include, but are not limited to, explosive hazards, fragments from explosions, and other operational hazards that occur during the course of military, police and other emergency service personnel missions. When sand or other fragments are projected off the ground from indirect impacts, the pants according to the invention provides protection from these fragments that may hit the wearer below the bullet resistant plate. Unlike prior art systems, the protective garment of the present invention provides an over garment shorts that can be worn on top of, or underneath, other protective garments and further, provides a continuous level of ballistic protection to the groin and pelvic regions of a wearer by providing ballistic panels in direct contact with these regions so that protection may be provided irrespective of the angle at which a harmful fragment approaches the wearer. For clarity, the term over garment shorts as are used throughout the description denotes a garment that may be worn over an underlying base layer and does not preclude the possibility of additional layers of protection being worn on top of the over garment shorts. The over garment shorts of the invention may be used with an emergency suit, a tactical suit and other protective garments that may or may not incorporate a bullet resistant plate.

Ballistic panels as incorporated into the invention in the manner described are not limited to particular forms of the ballistic panels. Materials for such panels are generally known in the art and the ballistic panels may be formed from any number of materials, including fabrics such as Aramid, ballistic resistant plastics, impact resistant materials and similar materials, such as Kevlar, and any combinations thereof that allow for ballistic resistance.

Figure 1:
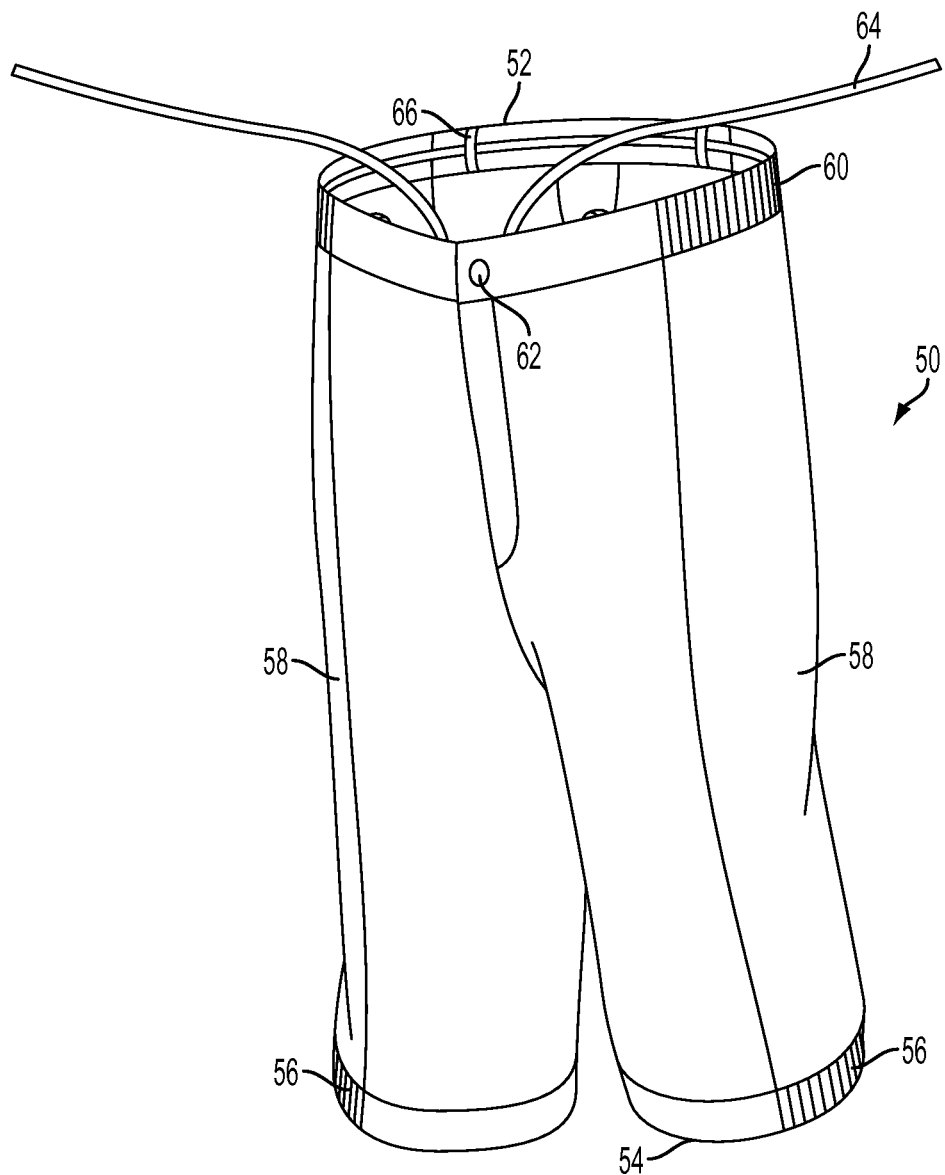
FIG. 1 is a front perspective view of one embodiment of the invention.
Figure 2:
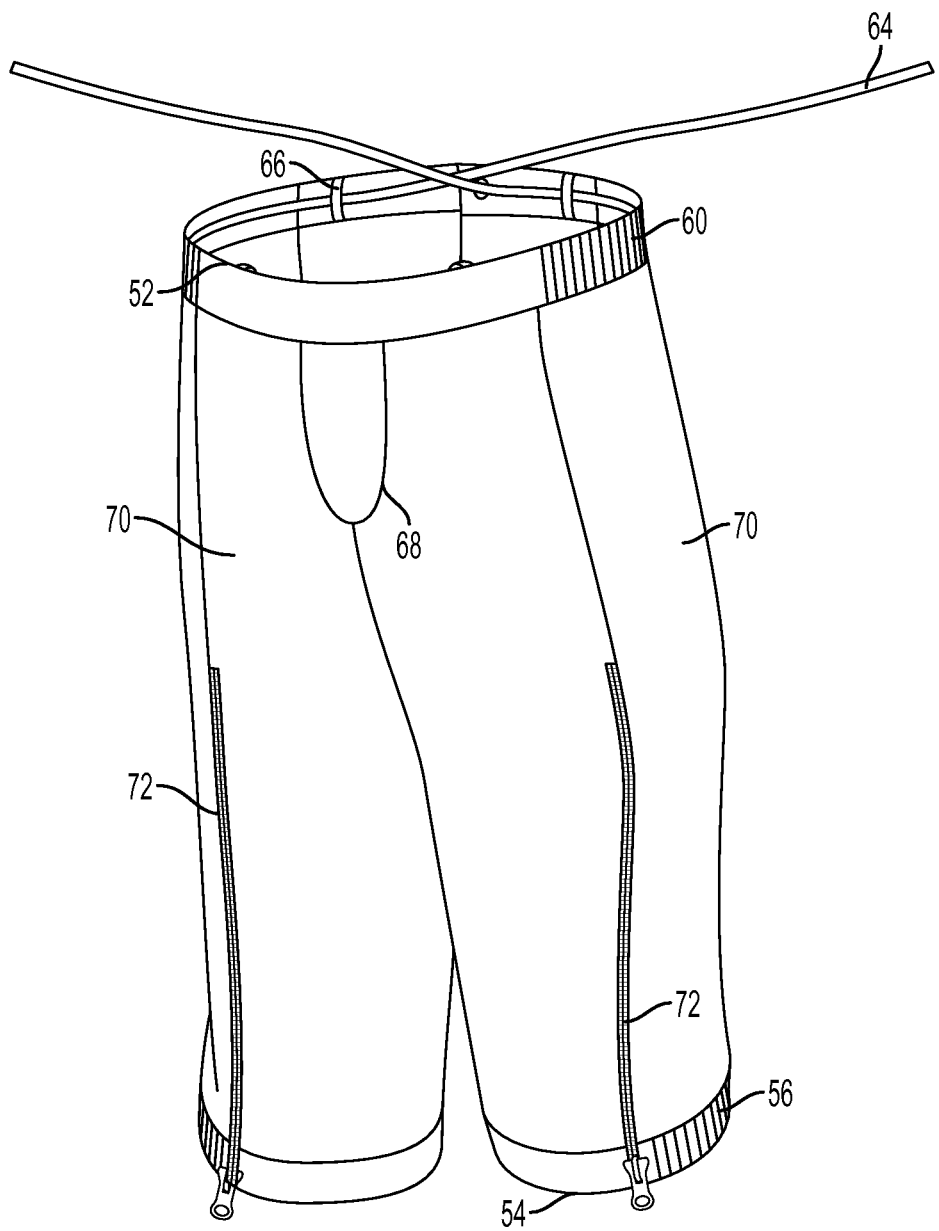
FIG. 2 is a rear perspective view of the embodiment of FIG. 1.
Figure 3:
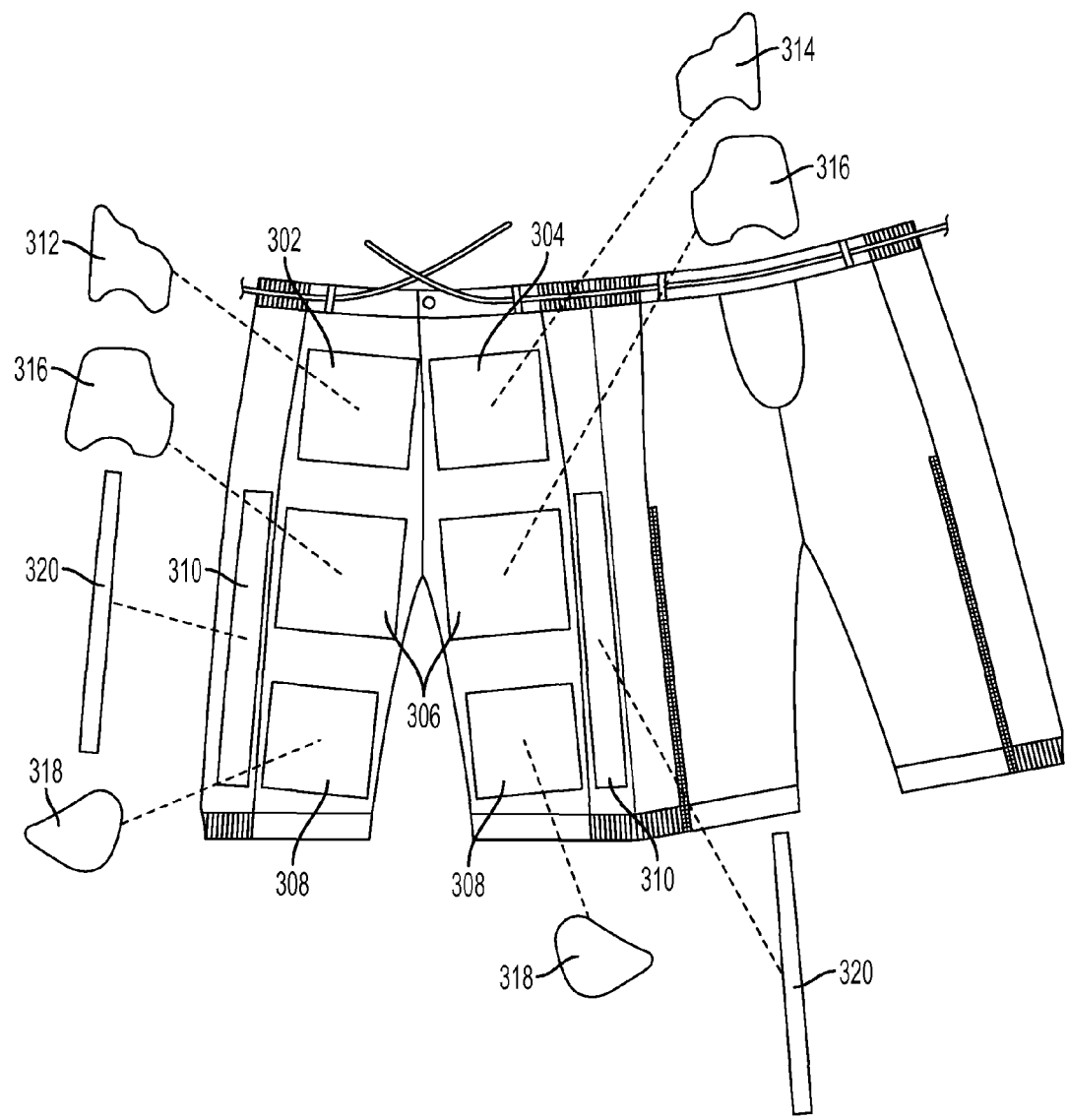
FIG. 3 is a plan view showing the interior of the embodiment of FIG. 1.

Referring now to FIGS. 1 to 3, there is shown one embodiment of the over garment shorts 50 according to the invention 1. The shorts generally include a top edge 52 that, when in use, would rest at a position above the pelvic bone of a wearer (not shown). The shorts are thus worn higher than typical pants or protective garments and extend to a lower edge 54 that extends to a position proximate the knee region of the wearer and preferably to a position approximately four inches below the knee of the wearer. In particular, the shorts are preferred to extend to cover the upper tibia below the knee in order to facilitate rehabilitation through modern prosthetics. That is, the use of modern prosthetics requires approximately four inches of bone extending to the upper tibia. Prior art protective shorts do not include this feature. It is preferably that the legs of the shorts taper inwards to create a close fit to the leg of the wearer, or to any underlying garment. At the lower edge 54, there is preferably provided an elastic cuff 56 to secure the lower edge 54 to the leg, and to prevent any fragmentary materials from being lodged under the shorts 50.

In some embodiments, the outer portion 58 of each leg is formed from an elastic material to accommodate different sizes, and different under garments. This is particularly helpful where the under garments themselves contain some degree of ballistic protection and would be larger than the wearer's bare leg size. A waistband 60 is provided proximate the top edge 52 of the short. The waistband may be closed by snap connectors 62 or buckles as are known in the art. Optionally, there is provided a drawstring 64 that acts as a waistband, and is provided entirely on an inner surface of the pants, supported by loops 66, for example. The drawstring 64 may be provided to ensure the shorts 50 rest above the pelvic bone of the wearer. A typical belt or various other forms of securing pants to a wearer may not be effective in this regard.

As shown in FIG. 2, the rear of the shorts 50 preferably includes an opening 68 extending from a position proximate the top edge 52 to a position above that at which the legs 70 of the shorts begin. The opening 68 provides for greater air flow to the wearer from a region in which the shorts are not intended to protect. Furthermore, this permits the entirety of the front of the shorts 50 to be manufactured from a ballistic resistant fabric. Some prior art protective garments provide for increased airflow by providing a portion of the material to be perforated, however, this precludes the ability of the material itself to provide a degree of ballistic resistance, particularly from small fragments such as sand. In the invention as herein described, the rear portions of the wearer may not be protected in the same manner and accordingly, the entirety of the front portion may be made from a ballistic resistant panel and the opening 68 as described provided in the rear.

The shorts according to the invention include at least one pocket, sized and otherwise dimensioned to removeably receive a ballistic protection panel there and at least one ballistic protection panel configured to fit within each of these pockets. Various arrangements of these pockets are contemplated by the invention, and are exemplified in the description that follows.

FIG. 3 shows one arrangement of a set of pockets, and corresponding ballistic panels that are designed to provide protection to the pelvic region, the groin region and portions of the leg region of the wearer. The set of pockets preferably includes at least one pocket 302 configured to overlap the sacrum region on the pelvis of the wearer and at least one pocket 304 configured to overlap each of the ilium regions on the pelvis of the wearer. It will be understood that FIG. 3 illustrates these regions schematically for ease of illustration and understanding of the invention. It will be understood that only some of the pockets in the set may be included.

The set of pockets may further include at least one inner thigh pocket 306 configured to overlap an inner thigh region of the wearer, and preferably two inner thigh pockets 306. There may further be provided at least one, and preferably two, outer thigh pockets 310 configured to overlap a region on the outer thigh of the wearer. Each of these pockets are also configured to receive ballistic panels 312, 314, 316, 318 and 320, respectively.

Generally, the set of pockets, and corresponding ballistic panels, are configured to cover each of the pelvic and groin regions of the wearer as it has been discovered that these regions are the most susceptible to damage from fragmentary impacts, such as from sand.

While it is contemplated that the pockets may be provided on either the interior or on the exterior surfaces of the pants, it is preferred that each of the pockets, and the ballistic panels provided therein are provided on the inside of the pants, as illustrated in FIG. 3. Providing the pockets and panels on the interior surface of the pants provides a safe and secure way for preventing damage to the pockets themselves, for example at the seams. Providing for removeable panels in the pockets as herein described and illustrated, allows the ballistic panels to be removed for washing, cleaning, replacement and/or mass transportation. The pockets may be enclosed by any means that would be apparent to a person skilled in the art, including but not limited to zippers and hook and loop fasteners. Furthermore, it is contemplated that a fastening means may be provided within each pocket to hold the ballistic panel in place within the pocket, for example to prevent such movement of the ballistic panel that may cause damage to the enclosing means on the pocket. In repeated use, this could result in the ballistic panel being displaced entirely during an incident. For example, one side of a hook and loop fastener may be provided on an interior surface of the pocket and the corresponding side of the hook and loop fastener provided on an underside of the ballistic panel.

The level of protection is provided by the ballistic resistant panels used in the shorts of the invention is predetermined by a contracting agency or wearer, and may be based on government guidelines and certification tests for different ballistic materials.

Figure 4:
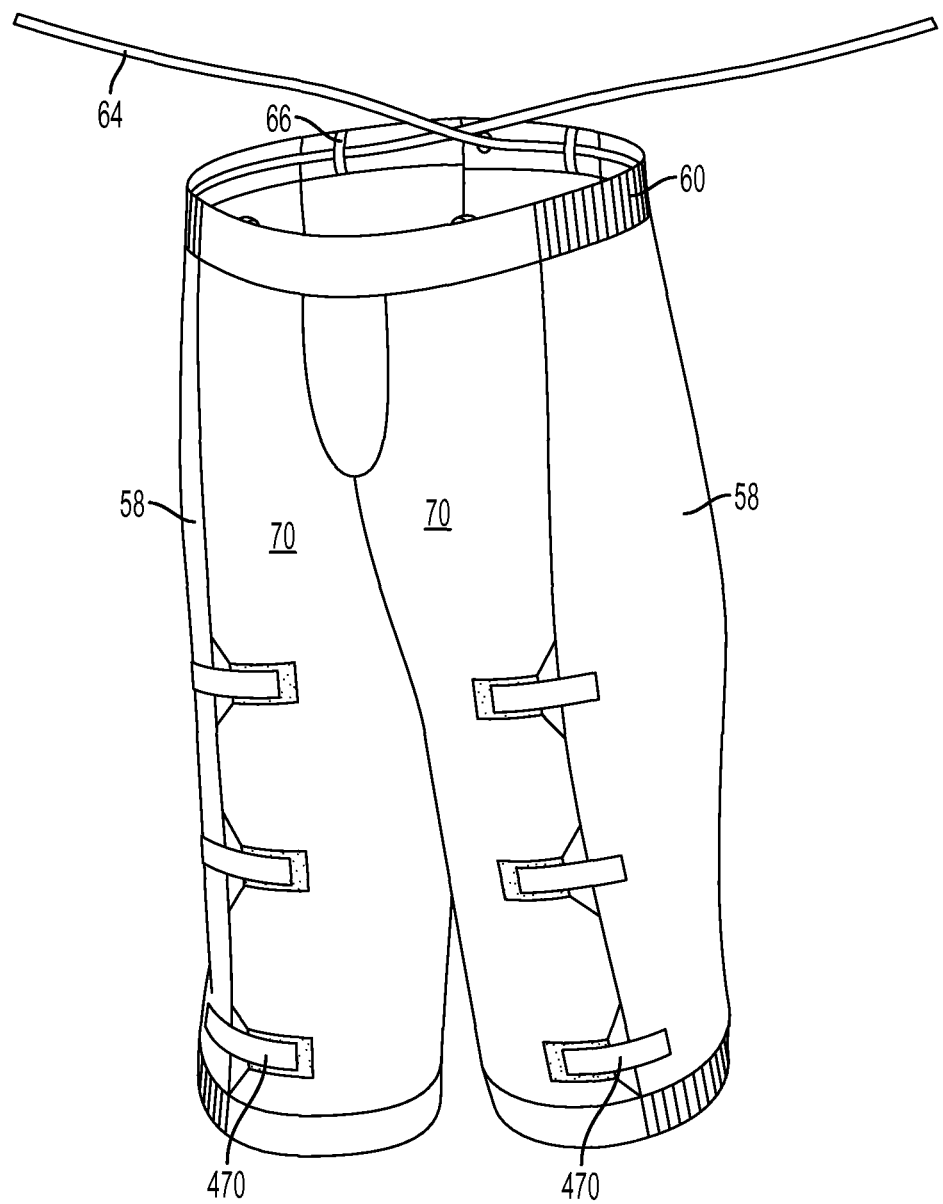
FIG. 4 is a rear perspective view of a variant of the embodiment of FIG. 1.
Figure 5:
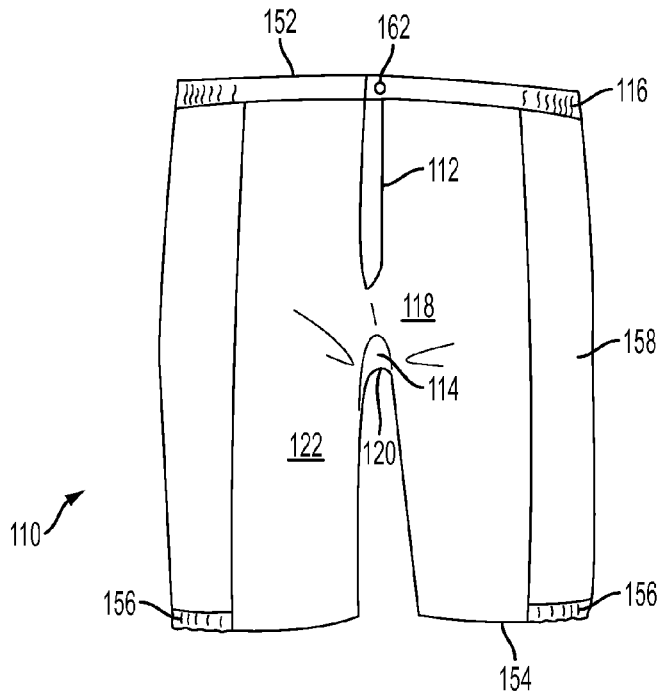
FIG. 5 is a front view of another embodiment of the invention.
Figure 6:
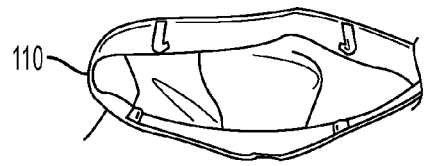
FIG. 6 is a top view of the embodiment of FIG. 5.
Figure 7:
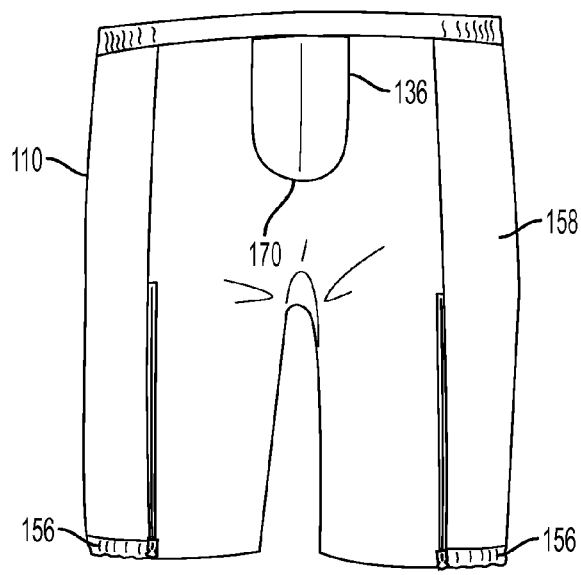
FIG. 7 is a rear view of the embodiment of FIG. 5.
Figure 8:
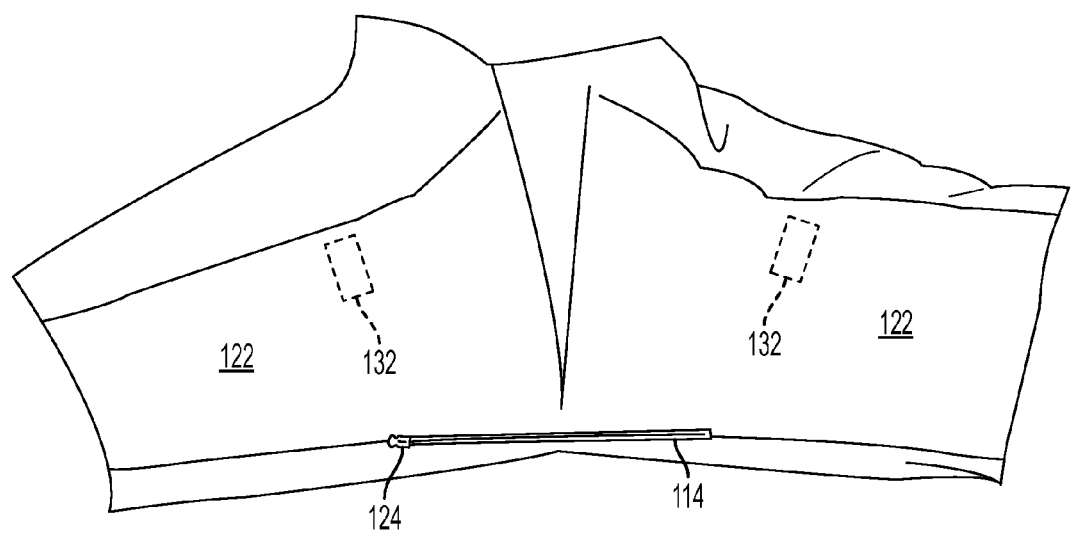
FIG. 8 shows the interior embodiment of FIG. 5.

The shorts according to the invention may further include a closing means provided on an outer seam of the shorts from a rear upper thing?? region through a bottom of the shorts to permit the wearer to don and/or doff the shorts while wearing boots; wherein said closing means is selected from the group consisting of a zipper, snap connectors, and hook and loop fasteners. In the embodiment of FIGS. 1-2, the closing means is a zipper provided on a rear leg portion of the pant, generally aligned with the hamstring of the wearer. An alternative embodiment is shown in FIG. 4, where buckle-type fasteners are used rather than the zippered closing. The provision of the closing means generally aligned with the hamstring portion of the wearer places such closing means in a position that mitigates the possible damage from fragments approaching from the front of the wear, thus limiting damage to the shorts in general.

Referring now to FIGS. 5 to 10, there is shown a preferred embodiment of the invention. The over garment shorts 110 generally include a top edge 152 that, when in use, would rest at a position above the pelvic bone of a wearer (not shown). The shorts are thus worn higher than typical pants or protective garments and extend to a lower edge 154 that extends to a position proximate the knee region of the wearer and preferably to a position approximately four inches below the knee of the wearer. It is preferably that the legs of the shorts taper inwards to create a close fit to the leg of the wearer, or to any underlying garment. At the lower edge 154, there is preferably provided an elastic cuff 156 to secure the lower edge 154 to the leg, and to prevent any fragmentary materials from being lodged under the shorts 110. In some embodiments, the outer portion 158 of each leg is formed from an elastic material to accommodate different sizes, and different under garments. This is particularly helpful where the under garments themselves contain some degree of ballistic protection and would be larger than the wearer's bare leg size. A waistband 116 is provided proximate the top edge 152 of the short. The waistband 116 may be closed by snap connectors 162 or buckles as are known in the art. The rear of the shorts 110, shown in FIG. 7 preferably includes an opening 136 extending from a position proximate the top edge 152 to a position above that at which the legs 170 of the shorts begin. The opening 168 provides for greater air flow to the wearer from a region in which the shorts are not intended to protect.

Over garment protective shorts 110 according to this embodiment includes a first pocket 112 and a second pocket 114 for receiving ballistic panels therein. First pocket 112 preferably extends from a position below the waistband 116 of the shorts 110 to below the groin region 118. Second pocket 114 is positioned on an underside 120 of the groin region between the inner thigh portions 122 of the shorts 110. This is shown clearly in FIG. 8, which shows the shorts 110 having been turned inside out. The second pocket 114 is provided on the interior position of the shorts 110 as illustrated, and is preferably closeable via zipper 124.

Figure 10:
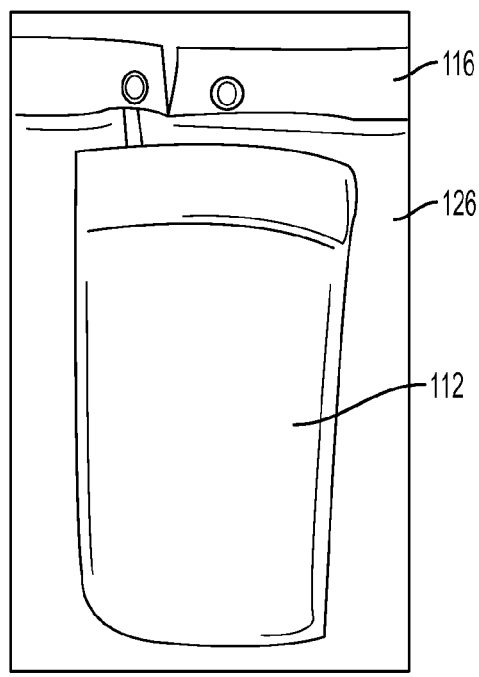
FIG. 10 is shows the interior of the fly region of the embodiment of FIG. 5.
Figure 11:
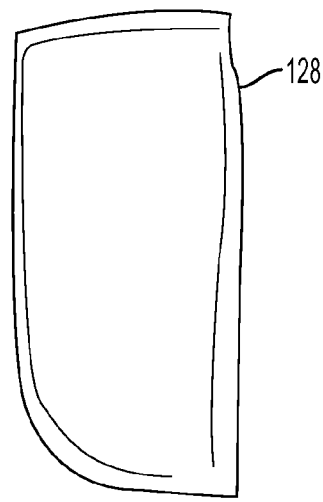
FIG. 11 is a front view of a ballistic panel for use at the fly region shown in FIG. 10.

FIG. 10 is a detail view of the fly portion 126 of the shorts 110, and in particular, an internal portion of the shorts 110. There is provided the first pocket 112 attachable to the interior surface of the pant 110 proximate the waistband 116. First ballistic panel 128 (shown in FIG. 11) is sized and otherwise dimensioned to fit snugly within the first pocket 112. In an embodiment, both the first pocket 112 and the first ballistic panel 128 are removable from the shorts so that both may be cleaned, either in combination or on their own. The first ballistic panel 128 is generally shaped to cover the entirety of the wearer's groin region.

Figure 9:
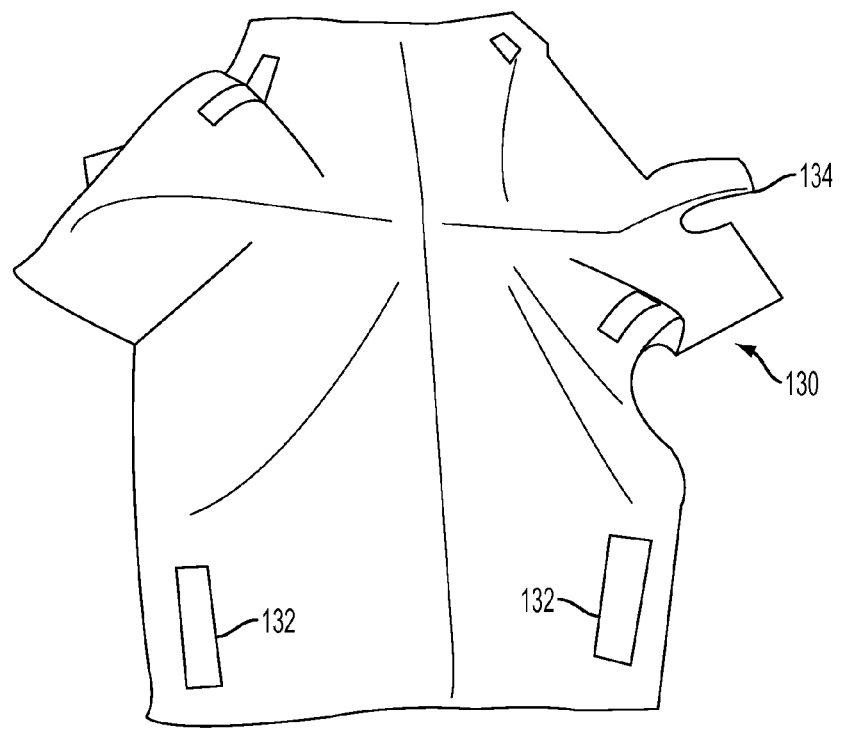
FIG. 9 is a front view of a ballistic panel for use with the embodiment of FIG. 5.

FIG. 9 shows a detail view of a second ballistic panel 130 arranged to be positioned within the second pocket 114. Second pocket 114 is substantially large and may provide access to the entirety of an interior region between and outer panel and an inner panel of the shorts 110. That is, the second pocket 114 may, in the alternative, be an opening into an interior region of the shorts 110. Second ballistic panel 130 is shaped and otherwise dimensioned to substantially cover the inner thigh region, groin region, and pelvic region of the wearer. The view in FIG. 10 is an expanded view of the second ballistic panel 130. In use, the ballistic panel 130 would be folded to fit within the shorts 110, in the shape of FIGS. 6 and 8, and extends through the inner thigh region, portions of the front and back of the legs and up towards the pelvic region. Corresponding sides of hook and loop fasteners 132 could be provided on the second panel 130 and on the interior of the second pocked 114, respectively, to hold the second ballistic panel 130 in position within the shorts 110.

In this embodiment, the second ballistic panel 130 may optionally be provided with a profiled, cut-out section 134 that corresponds with the opening 136 in the rear of the shorts (shown in FIG. 7) that provides for ventilation to the wearer.

The second ballistic panel 130 may take on variations in shape compared to that as illustrated, but in general, is understood to be a generally flexible ballistic panel that can be positioned within the interior of the second pocket to cover any one of the inner thigh region, the groin region, the pelvic region, the front leg region, the back leg region or any combination of same. It will also be understood that the second ballistic panel 130 is removeable from the shorts 110 via the second pocket 114.

Figure 12:
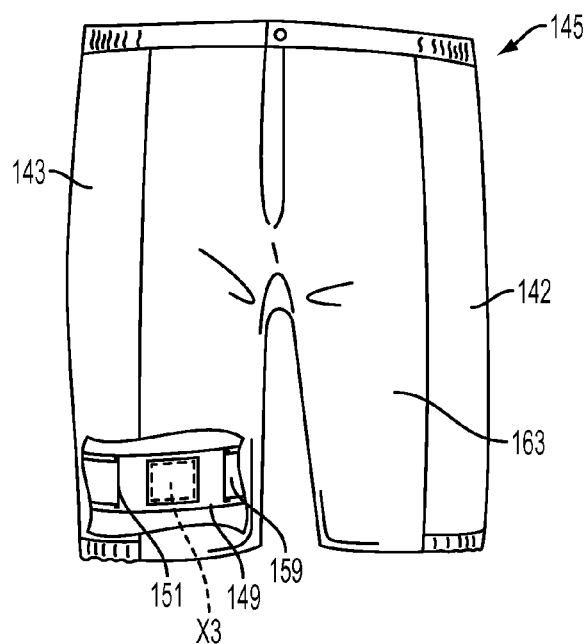
FIG. 12 is a front view of the embodiment of FIG. 1 incorporating the tourniquet members according to the invention.
Figure 13:
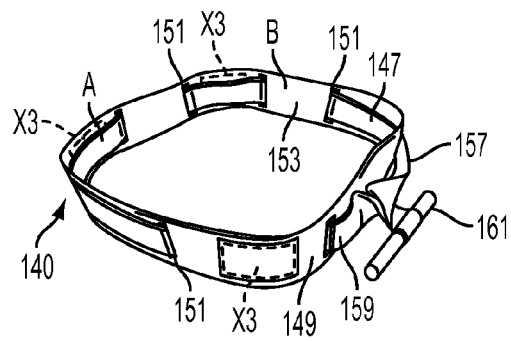
FIG. 13 is a detail view of the tourniquet member of FIG. 12.
Figure 14:
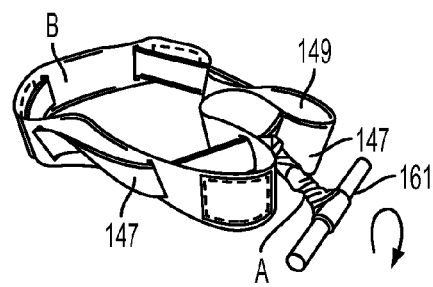
FIG. 14 is a detail view of a compressed tourniquet member of FIG. 13.

Referring now to FIGS. 12, 13 and 14, there is shown another embodiment of the invention in which the protective shorts described above further include one or more integrated tourniquet members 140. Preferably, there are two tourniquet members 140, one provided in each leg portion 142, 143 of the shorts 145. Each of the tourniquet members 140 preferably includes an inner strap 147 and an outers strap 149. The outer strap 149 preferably includes a series of loop openings 151 thorough which the inner strap 147 is interwoven. That is, the inner strap 147 is arranged such that it passes repeatedly from an interior surface 153 of the outer strap 149 to an exterior surface 155 of the outer strap 149. The outer strap 149 forms a closed loop, with first and second end portions 157, 159 of the inner strap 147 extending through the exterior surface of the outer strap 149 via a pair of the loop openings 151. The end portions 157, 159 of the inner strap 147 attach to a tightening means such as handle member 161 exterior to the outer strap 149. The handle member 161 is adapted to permit a user to grab onto and apply a twisting motion to the handle 161, as will be described below. The handle member 161 may be a rod around which the end portions 157, 159 loop and secure to. The tightening means may include any element that may be twisted to reduce the circumference of the inner strap 147. Other examples of the tightening means include a strap and buckle arrangement, other non-circular rod-like members, a drawstring, etc.

Each of the inner 147 and outer 149 straps are preferably formed from a webbing material that has predetermined elastic properties that can fit snuggly over a user's leg. The tourniquet members 140 are preferably attached onto an inside lining, or other inner surface, of the protective shorts above a portion of the shorts that would rest proximate the knee of the user. That is, the tourniquet members 140 are fixed to the shorts at an upper leg portion 163. Each of the tourniquet members 140 may be attached to the shorts by stitching the outer strap 149 to inner material on the shorts. Alternatively, hook and loop fasteners may be used to attach the outer strap 149 to the inside of the shorts, where one of the hook and loop fastener portion is attached to the outer strap 149 and the other of the hook and loop fastener portion is attached to the shorts. It should be noted that the outer strap 149 may be fixed to the shorts, but the inner strap 147 is unrestricted in its movement, except insofar as the inner strap 147 is looped through the outer strap 149 as described above.

In use, following the onset of an event causing an injury to the wearer's leg, the wearer (or another person assisting the wearer) twists the handle 161 whereby the circumference of the inner strap 147 is reduced with respect to the circumference of the outer strap 149 by virtue of the interwoven arrangement between the two straps that is described above. Accordingly, the inner strap 147 tightens around the lower thigh region of the wearer as the circumference of the inner strap 147 is reduced. The general operation of mitigating the damage from an injury using a tourniquet is known in the art, and not described in further detail herein. The wearer may access the handle 161 through either the interior of the shorts proximate the waist portion, or by having the handle extend close to the bottom of the shorts, whereby it is reachable proximate the knee region of the wearer.

In embodiments where the outer strap 149 is connected in a removable manner to the shorts, for example by using a hook and loop fastener, the outer strap 149 may also be adapted to detach from the shorts as the inner strap 147 is tightened. In this manner, if the shorts have to be removed from the wearer, this can be done without affecting the operation of the tourniquet members. In embodiments where the tourniquet members are attached to the shorts by stitching the outer strap 149 to an inner surface of the shorts, it is also possible to implement a relatively weak stitch that is designed to break upon tightening of the inner strap 147. In this manner, the shorts also become detachable from the tourniquet members altogether, particularly when the inner strap 147 has been tightened to mitigate the damage of an injury.

Furthermore, it is also contemplated that embodiments of the invention making use of the integrated tourniquet members may further be extended to an application where full length protective pants are used, rather than the protective shorts as described in the representative examples above. In this embodiment, the handle of the tourniquet members will generally only be accessible via the interior of the pants from the waist portion. In any event, the operation and benefits as described are directly analogous.

Other modifications and alterations may be used in the design and manufacture of other embodiments according to the present invention without departing from the spirit and scope of the invention, which is limited only by the accompanying claims.

We claim:

1. A protective garment comprising:
   a waist portion adapted to be donned proximate the waist of a wearer and first and second leg portions extending from a waist portion to at least proximate a knee portion of the wearer;
   a tourniquet member attached to an inner surface of at least one of said first and second leg portions;
      wherein said tourniquet member comprises:
         an outer strap formed into a closed loop and having a plurality of loop openings;
         an inner strap interwoven through said plurality of loop openings;
         tightening means for reducing a circumference of said inner strap such that said inner strap tightens around a portion of the leg of the wearer.

2. A protective garment according to claim 1, wherein said tightening means comprises a handle member and said inner strap includes first and second ends extending from respective loop openings on said outer strap and fixed to said handle member; whereby twisting of said handle member results in said reducing of said circumference of said inner strap.

3. A protective garment according to claim 1, wherein said tourniquet member is removably attached to said inner surface.

4. A protective garment according to claim 3, wherein said tourniquet member detaches from said inner surface upon tightening of said inner strap.

5. A protective garment according to claim 4, wherein said tourniquet member is attached to said inner surface using one of stitching and hook and loop fasteners.

6. A protective garment according to claim 1, further comprising
   at least one pocket sized and otherwise dimensioned to removeably receive a ballistic protection panel therein;
   at least one ballistic protection panel configured to fit within each of said at least one pockets;
   wherein said protective garment is configured to be worn over existing pants and extend from a position covering the pelvic region of a wearer to a position proximate the knee region of the wearer.

7. A protective garment according to claim 6, wherein said at least one pocket comprises two pockets and said at least one ballistic protection panel comprises two panels configured to fit within said two pockets; wherein said two pockets include:
   i. a first pocket configured to overlap the groin region of the wearer;
   ii. a second pocket having an opening on an underside of the groin region of the wearer; said second pocket extending substantially across an inner thigh region of the wearer and up to the pelvic region of the wearer.

8. A protective garment according to claim 7, wherein said two panels include:
   i. a first panel configured to fit within said first pocket and overlap the groin region of the wearer;
   ii. a second panel configured to fit within said second pocket; wherein said second panel is sized and otherwise dimensioned to extend across the inner thigh region of the wearer and around the buttocks region of the wearer.

9. A protective garment according to claim 8, wherein said second pocket includes at least one first portion of a hook and loop fastener and said second pocket includes at least one second portion of a hook and loop fastener to attach said second panel in a fixed position within said second pocket.

10. A protective garment according to claim 8, wherein said second panel is a flexible panel configured to be positioned across the inner thigh regions of a wearer and over a portion of the front and back portions of the leg of a wearer.

11. A protective garment according to claim 8, wherein said second panel extends to overlap the sacrum and ilium regions of the wearer.

12. A protective garment according to claim 6, wherein said position proximate the knee comprises a position approximately four inches below the knee covering the upper tibia of the knee.

13. A protective garment according to claim 6, wherein each of said pockets are provided on an interior surface of the shorts.

14. A protective garment according to claim 6, further comprising a waistband supported by inner belt loops formed on an interior surface of the shorts, proximate a top region of the shorts.

15. A protective garment according to claim 6, further comprising a closing means on an outer seam from a rear upper thigh region through a bottom of the shorts to permit the wearer to don and/or doff the shorts while wearing boots; wherein said closing means is selected from the group consisting of a zipper, snap connectors, and hook and loop fasteners, and wherein said closing means is generally aligned with the hamstring of the wearer.

16. A protective garment according to claim 6, further comprising elastic cuffing on a bottom side panel.

17. A protective garment according to claim 8, further comprising an opening in the rear of the pants permitting increased airflow to the wearer.

18. A protective garment according to claim 17, wherein said opening extends from a position proximate a top edge of the shorts to a position proximate the tailbone of the wearer.

19. A protective garment according to claim 18, wherein said second panel has an opening formed therein corresponding with said opening in the shorts and said second panel otherwise extends across the entire inner thigh and pelvic region of the wearer.

20. A protective garment according to claim 6, wherein said at least one pocket includes a set of pockets and said at least one ballistic protection panel includes a corresponding set of ballistic protection panels; said set of pockets comprises:
  i. at least one sacrum pocket configured to overlap the sacrum region of the wearer;
  ii. a least one ilium pocket configured to overlap each ilium region of the wearer.

21. A protective garment according to claim 20, wherein said set of pockets further comprises:
  iii. at least one inner thigh pocket configured to overlap an inner thigh region of the wearer.

22. A protective garment according to claim 20, wherein said set of pockets further comprises:
  iv. at least one outer thigh pocket configured to overlap an outer thigh region of the wearer.

23. A protective garment according to claim 20, further comprising a closing means on an outer seam from a rear upper thigh region through a bottom of the shorts to permit the wearer to don and/or doff the shorts while wearing boots; wherein said closing means is selected from the group consisting of a zipper, snap connectors, and hook and loop fasteners.

* * * * *